United States Patent
Chuang (10) Patent No.: US 12,383,598 B2
(45) Date of Patent: Aug. 12, 2025

(54) METHOD FOR TREATING GINGIVITIS AND GINGIVAL ATROPHY AND REPAIRING ORAL MUCOSA

(71) Applicant: ADVANCED HEALTHTECH BIOPEPTIDE LABORATORIES CO., LTD, Taichung (TW)

(72) Inventor: Ko-Sheng Chuang, Taichung (TW)

( * ) Notice: Subject to any disclaimer, the term of this patent is extended or adjusted under 35 U.S.C. 154(b) by 0 days.

(21) Appl. No.: 18/048,025

(22) Filed: Oct. 19, 2022

(65) Prior Publication Data

US 2023/0293625 A1    Sep. 21, 2023

(30) Foreign Application Priority Data

Oct. 20, 2021    (CN) .......................... 202111222709.2

(51) Int. Cl.
*A61K 38/08* (2019.01)
*A61K 38/07* (2006.01)
*A61P 1/02* (2006.01)

(52) U.S. Cl.
CPC .............. *A61K 38/08* (2013.01); *A61K 38/07* (2013.01); *A61P 1/02* (2018.01)

(58) Field of Classification Search
CPC ............ A61K 38/08; A61K 38/07; A61P 1/02
See application file for complete search history.

(56) References Cited

FOREIGN PATENT DOCUMENTS

| CN | 109833266 A | * | 6/2019 | |
| TW | I432206 B | | 4/2014 | |
| TW | I448306 B | | 8/2014 | |
| TW | 201538729 A | | 10/2015 | |
| TW | 201806602 A | | 3/2018 | |
| TW | I631141 B | | 8/2018 | |
| WO | WO-2021170064 A1 | * | 9/2021 | ............... A61K 8/19 |

OTHER PUBLICATIONS

Merriam Webster dictionary: Lotion, 2025 https://www.merriam-webster.com/dictionary/lotion, last visited Mar. 6, 2025.*
Medline Plus, Gingivitis, Medical Encyclopedia, https://medlineplus.gov/ency/article/001056.htm; last visited Mar. 6, 2025.*
National Library of Medicine, Using Medications: Topical Medications, Aug. 2021; See p. 1; https://www.ncbi.nlm.nih.gov/books/NBK361003/.*

* cited by examiner

*Primary Examiner* — Jeanette M Lieb
(74) *Attorney, Agent, or Firm* — Bruce Stone LLP; Joseph A. Bruce (57) ABSTRACT

The present invention relates to a method for treating gingivitis and gingival atrophy and repairing oral mucosa in a subject, comprising a step of administering to the subject a therapeutically effective amount of an oligopeptide of the formula (I):

$$X_1X_2X_3X_4X_5X_6 \quad (I)$$

wherein
$X_1$ is glycine (Gly; G) or lysine (Lys; K);
$X_2$ is glutamic acid (Glu; E) or threonine (Thr; T);
$X_3$ is K or T;
$X_4$ is G or K;
$X_5$ is serine (Ser, S), phenylalanine (Phe; F) or absent; and
$X_6$ is F or absent.

3 Claims, 13 Drawing Sheets
Specification includes a Sequence Listing.

| Before administration of the gingiva-repairing lotion. | 1 month after administration of the gingiva-repairing lotion. | 6 months after administration of the gingiva-repairing lotion. |
|---|---|---|
|  |  |  |

Figure 11

METHOD FOR TREATING GINGIVITIS AND GINGIVAL ATROPHY AND REPAIRING ORAL MUCOSA

The contents of the electronic sequence listing (ST26.xml; Size: 4,466 Bytes; and Date of Creation: Nov. 24, 2023) is herein incorporated by reference in its entirety.

TECHNICAL FIELD OF THE INVENTION

The present invention relates to the field of pharmaceuticals, and particularly a method of using an oligopeptide for treating gingivitis and gingival atrophy and repairing oral mucosa.

BACKGROUND

TW 1448306 B discloses an oral care composition comprising an effective amount of a basic amino acid in free or salt form and a low dosage of fluoride.

TW 1432206 B discloses an oral care composition comprising a combination of extracts comprising a mixture of extracts from at least three of Punica granatum, *Myristica fragrans, Zingiber officinale*, and Zizyphus joazeiro and a natural extract other than the extract from at least three of Punica granatum, *Myristica fragrans, Zingiber officinale*, and Zizyphus joazeiro, and an orally acceptable carrier, wherein the composition comprises 0.01% to 5% by weight of the combination of extracts.

TW 201538729 A discloses a composition and method utilizing hair follicle derived Non-Bulbar Dermal Sheath (NDBS) cells for the treatment of dental-related conditions, including the treatment of gingivitis.

TW 1631141 B discloses use of an oligopeptide consisting of 6 amino acids for treating conditions in oral mucosa, wherein both N and C terminus of the oligopeptide are substituted.

TW 201806602 A discloses an inflammation and sore resistant medicine for oral soft tissue (gum, mucous membrane), which is a mixture containing one or more adrenocorticotropic hormones or anti-inflammatory inhibiting compounds, one or more adhesive polymers having long term adhesion, one filling and repairing agent, and one or more additives.

There was no teaching or suggestion in prior arts that an unsubstituted oligopeptide consisting of 4, 5 or 6 amino acids could be effective in treating gingivitis and gingival atrophy and repairing oral mucosa.

DESCRIPTION OF THE INVENTION

The present invention discloses a method for treating gingivitis and gingival atrophy and repairing oral mucosa in a subject, comprising a step of administering to the subject a therapeutically effective amount of an oligopeptide of the formula (I):

$$X_1X_2X_3X_4X_5X_6 \quad (I)$$

wherein
$X_1$ is glycine (Gly; G) or lysine (Lys; K);
$X_2$ is glutamic acid (Glu; E) or threonine (Thr; T);
$X_3$ is K or T;
$X_4$ is G or K;
$X_5$ is serine (Ser; S), phenylalanine (Phe; F) or absent; and
$X_6$ is F or absent.

In an embodiment, the oligopeptide of the formula (I) is GEKGF and/or GEKG.

In a preferred embodiment, the oligopeptide of the formula (I) is GEKG.

In another embodiment, the oligopeptide of the formula (I) is KTTKS and/or KTTKSF.

In another preferred embodiment, the oligopeptide of the formula (I) is KTTKS.

In a further embodiment, the oligopeptide of the formula (I) is a combination of GEKG with KTTKS.

In a further embodiment, 0.1 to 10% by weight of GEKG and 0.1 to 10% by weight of KTTKS are administered. In a further preferred embodiment, 0.2 to 2% by weight of GEKG and 0.2 to 2% by weight of KTTKS are administered.

In a further embodiment, the oligopeptide of the formula (I) is formulated in a form of powder, aerosol, ointment, gel, paste or solution. The pharmaceutically acceptable carrier or excipient, which may be in a form of solid, semi-solid or liquid, for preparing the powder, aerosol, ointment, gel, paste or solution, and an amount thereof, have been well known and conventionally used in the art.

In a further preferred embodiment, the oligopeptide of the formula (I) is formulated in an aqueous buffer, including but not limited to a phosphate or citrate buffer.

In a further embodiment, the oligopeptide of the formula (I) is administered orally, including but not limited to administration via mucosal absorption or oral absorption.

In a further preferred embodiment, the oligopeptide of the formula (I) is of sustained release via mucosal absorption or oral absorption.

In an embodiment, oligopeptides GEKG or GEKGF and KTTKS or KTTKSF can be prepared in accordance with the teaching of prior arts, such as the method disclosed in TW 201129368 A1 and TW 201333045 A1.

EXAMPLES

Example 1. Evaluation of GEKG and KTTKS in TNFα Inhibition and cytotoxicity to L929 Cells In Vitro In vitro L929 cell proliferation/cytotoxicity assay was measured in a microtiter plate. L929 cells were cultured in the Eagle's minimum essential medium (EMEM) containing 10% bovine serum, 1% P/S and 1% non-essential amino acids. Converged L929 cells were washed by 2 ml of a phosphate buffer solution (PBS) and then treated with trypsin, followed by resuspension in the EMEM. 200 μl of the cell suspension were taken by suction for cell density counting, and the remaining cell suspension were centrifuged at 1500 rpm for 5 minutes. The supernatant was removed, and the EMEM was added for diluting the cells to form a final concentration of $1.5 \times 10^5$ cells/ml. 100 μl of the resultant cell suspension were added to each well of a 96-well flat-bottom microtiter plate, and then incubated at 37° C. and 5% $CO_2$ for 24 hours.

TNFα Inhibition

GEKG and KTTKS were re-solved with 1× PBS to form solutions having a concentration equivalent to 1 mg GEKG/ml and 1 mg KTTKS/ml, respectively, followed by further dilution with 1× PBS to form solutions having a concentration of 500, 125, 31.25 and 7.81 μg GEKG/ml and solutions having a concentration of 500, 125, 31.25 and 7.81 μg KTTKS/ml, respectively, and the resultant diluted solutions were mixed with a TNFα solution with an equal volume, and incubated for 1 hour. 50 μl of each of the 4 mixtures were added to the above 96-well flat-bottom microtiter plate containing L929 cells incubated for 24 hours, and actinomycin D (ActD) with a final concentration of 2 μg/ml and TNFα with a final concentration of 0.1 ng/ml were added to each well. Test wells containing 2 μg/ml ActD only and 0.1 ng/ml TNFα only were used as positive controls and blank controls, respectively. The resultant 96-well flat-bottom microtiter plate was further incubated at 37° C. and 5% $CO_2$ for 24 hours. O.D. values at 490/630 nm were measured by a microplate reader. TNFα inhibition was calculated by the following formula:

$$TNF\alpha \text{ inhibition } (\%) = \frac{OD_{diluent+TNF\alpha+Act} - OD_{TNF\alpha+Act}}{OD_{Act} - OD_{TNF\alpha+Act}} \times 100\%$$

Cytotoxicity

GEKG and KTTKS were re-solved with 1× PBS to form solutions having a concentration equivalent to 1 mg GEKG/ml and 1 mg KTTKS/ml, respectively, followed by further dilution with 1× PBS to form solutions having a concentration of 500, 125, 31.25 and 7.81 μg GEKG/ml and solutions having a concentration of 500, 125, 31.25 and 7.81 μg KTTKS/ml, respectively. 50 μl of each of the 4 diluted solutions were added to the above 96-well flat-bottom microtiter plate containing L929 cells incubated for 24 hours, and ActD with a final concentration of 2 μg/ml was added to each well. The resultant 96-well flat-bottom microtiter plate was further incubated at 37° C. and 5% $CO_2$ for 24 hours, followed by addition of 50 μl of 2,3-bis(2-methoxy-4-nitro-5-sulfophenyl)-5-[(phenylamino)carbonyl]-2H-tetrazolium hydroxide (XTT) to each well and further incubation for 1 hour. O.D. values at 490/630 nm were measured by a microplate reader. Cytotoxicity was calculated by the following formula:

$$\text{Cytotoxicity } (\%) = (1 - \frac{OD_{diluent+Act}}{OD_{ActD}}) \times 100\%$$

Results

Figure 1:
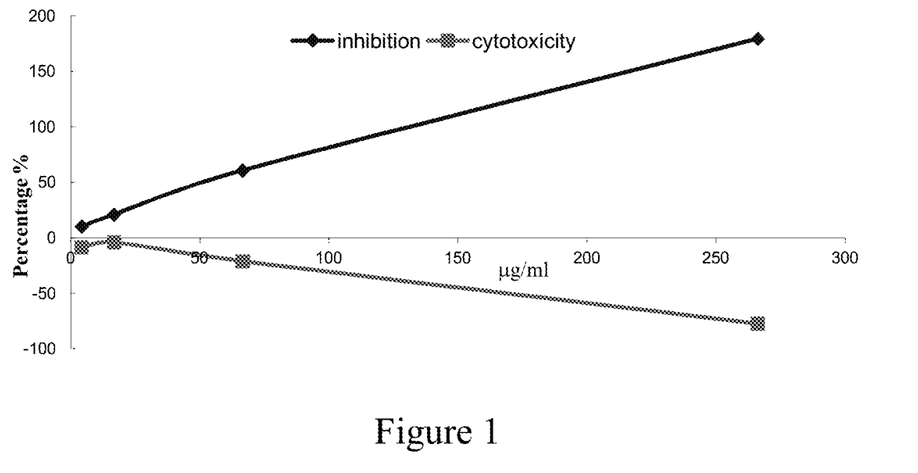
FIG. 1 shows tumor necrosis factor-alpha (TNFα) inhibition and cytotoxicity to L929 cells of KTTKS in a series of dilutions.

FIG. 1 shows TNFα inhibition and cytotoxicity to L929 cells of KTTKS in a series of dilutions. TNFα inhibition (%) of KTTKS is 179.4%, indicating that KTTKS exhibits a superior effect in TNFα inhibition and does not induce cytotoxicity.

TABLE 1

| KTTKS (μg/ml) | O.D. | Inhibition (%) | O.D. | Cytotoxicity (%) |
|---|---|---|---|---|
| 266 | 2.363 | 179.4 | 2.616 | −77.1 |
| 66.5 | 1.042 | 60.9 | 1.784 | −20.8 |
| 16.625 | 0.597 | 21.1 | 1.535 | −3.9 |
| 4.156 | 0.479 | 10.5 | 1.600 | −8.3 |

Figure 2:
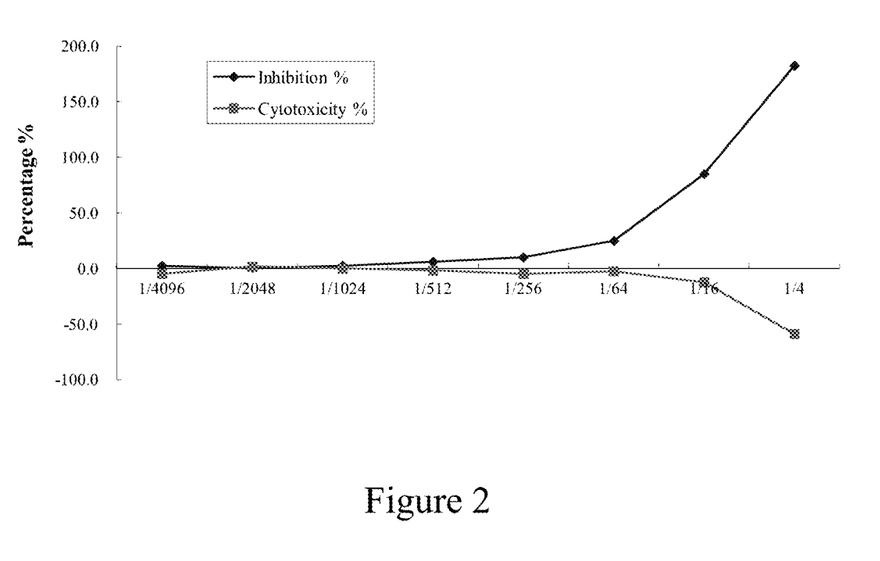
FIG. 2 shows TNFα inhibition and cytotoxicity to L929 cells of GEKG in a series of dilutions.

FIG. 2 shows TNFα inhibition and cytotoxicity to L929 cells of GEKG in a series of dilutions. TNFα inhibition (%) of GEKG is 182.3%, indicating that GEKG exhibits a superior effect in TNFα inhibition and does not induce cytotoxicity.

TABLE 2

| GEKG dilution | O.D. | Inhibition (%) | O.D. | Cytotoxicity (%) |
|---|---|---|---|---|
| 1/4 | 2.87 | 182.3 | 2.84 | −58.74 |
| 1/16 | 1.60 | 85.2 | 2.01 | −12.27 |
| 1/64 | 0.80 | 25.0 | 1.83 | −2.32 |
| 1/256 | 0.61 | 10.1 | 1.87 | −4.61 |
| 1/512 | 0.56 | 6.3 | 1.82 | −1.71 |
| 1/1024 | 0.51 | 2.6 | 1.79 | 0.11 |
| 1/2048 | 0.48 | 0.5 | 1.75 | 1.90 |
| 1/4096 | 0.51 | 2.5 | 1.87 | −4.72 |

Example 2. Evaluation of Free Radical Nitric Oxide (NO)-Capturing Anti-Inflammation of GEKG and KTTKS by Inhibiting Production of NO from Macrophages in the Presence of Inflammation-Inducing Lipopolysaccharide (LPS) In Vitro In vitro anti-inflammation of GEKG and KTTKS was evaluated by using the well-known inflammation model of NO production from macrophages induced by lipopolysaccharide (LPS).

Figure 3:
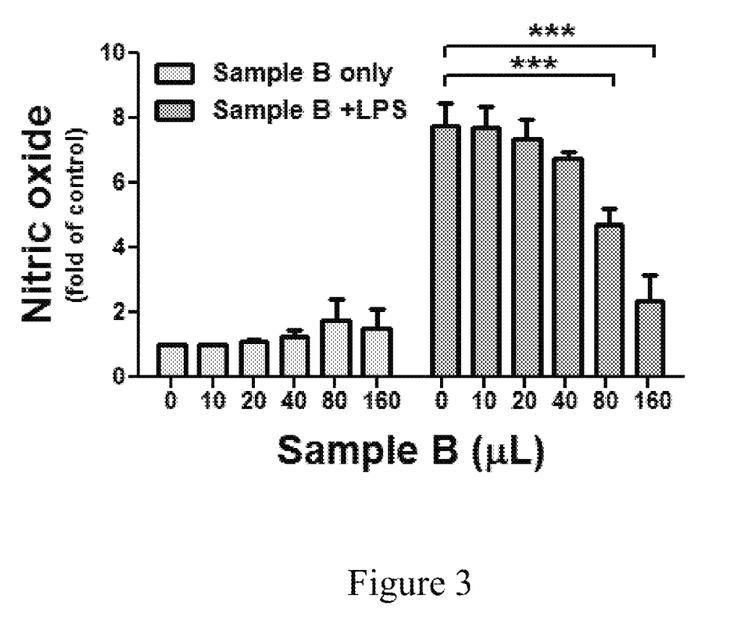
FIG. 3 shows inhibition of KTTKS in the production of nitric oxide (NO) from macrophages in the presence of inflammation-inducing lipopolysaccharide (LPS).
Figure 4:
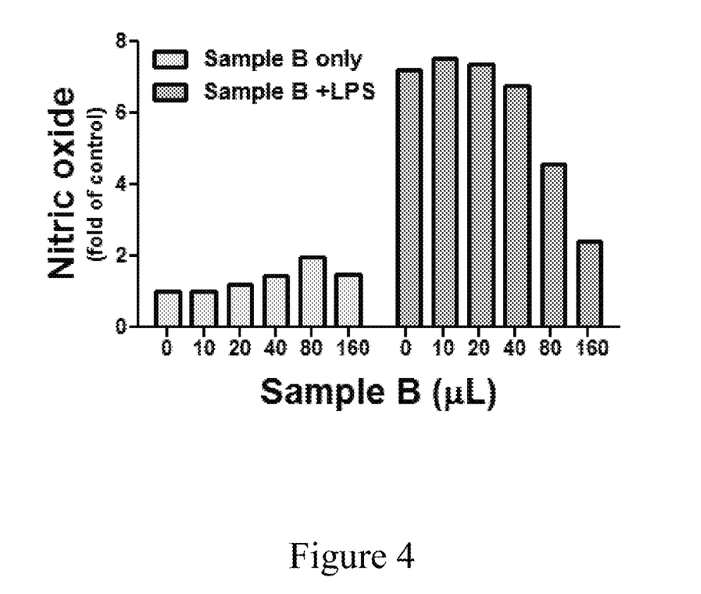
FIG. 4 shows inhibition of GEKG in the production of NO from macrophages in the presence of inflammation-inducing LPS.

Experimental result of anti-inflammation of KTTKS and GEKG were shown in FIGS. 3 and 4, respectively, which demonstrate that both KTTKS and GEKG inhibit NO production from macrophages induced by LPS in a dose-dependent manner.

Example 3. Evaluation of Hydrogen Peroxide ($H_2O_2$)-Capturing GEKG and KTTKS against inflammatory oxidation pressure by inhibiting production of $H_2O_2$ from Macrophages in the Presence of Inflammation-Inducing Lipopolysaccharide (LPS) In Vitro An ability of GEKG and KTTKS against inflammatory oxidation pressure in vitro was evaluated by using the well-known inflammation model of $H_2O_2$ production from macrophages induced by lipopolysaccharide (LPS).

Figure 5:
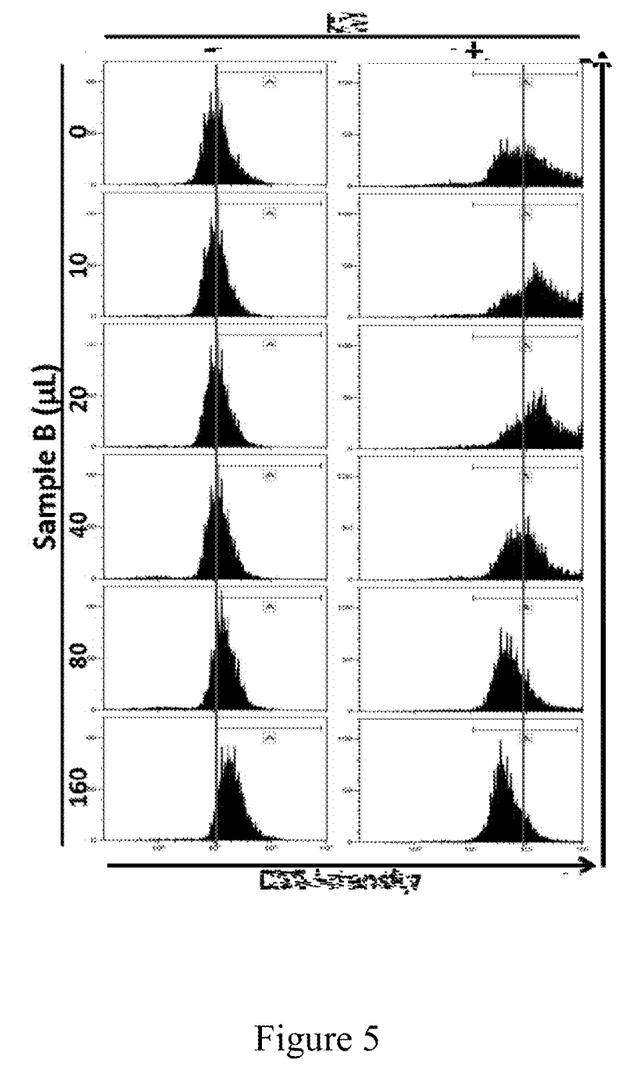
FIG. 5 shows inhibition of GEKG and KTTKS in the production of hydrogen peroxide ($H_2O_2$) from macrophages in the presence of inflammation-inducing LPS.

Experimental result of KTTKS and GEKG against inflammatory oxidation pressure were shown in FIG. 5, which demonstrates that both KTTKS and GEKG inhibit $H_2O_2$ production from macrophages induced by LPS in a dose-dependent manner.

Figure 6:
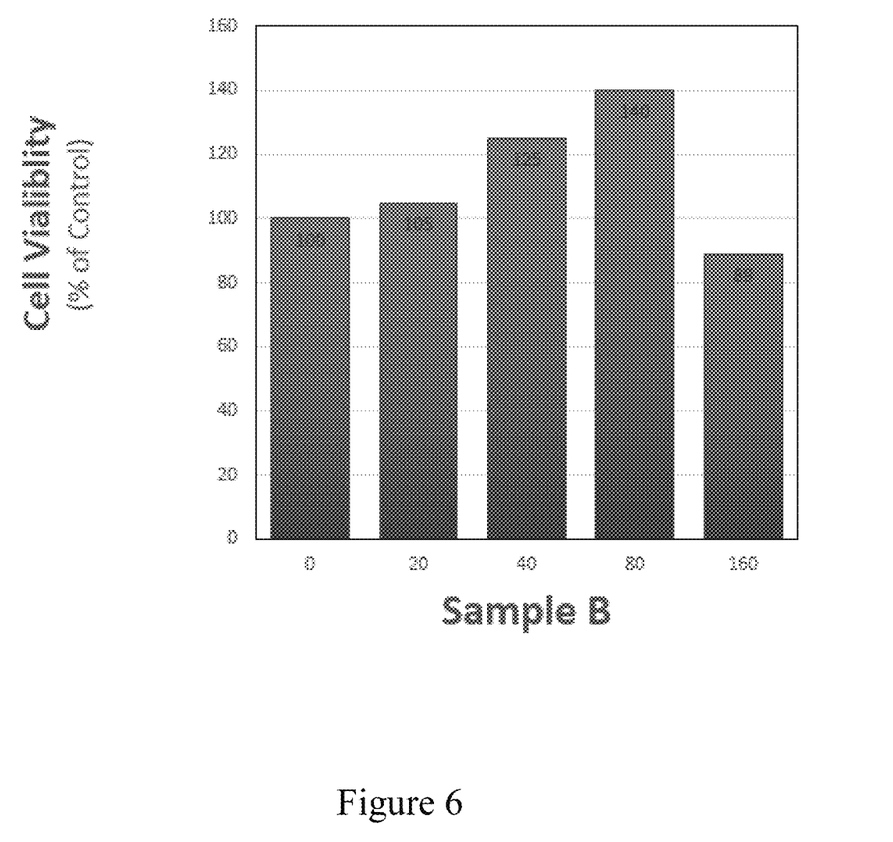
FIG. 6 shows an effect of GEKG and KTTKS in different concentrations in promoting proliferation of primary oral epithelial cells.

Example 4. Evaluation of GEKG and KTTKS in Promoting Proliferation of Primary Oral Epithelial Cells FIG. 6 shows that both GEKG and KTTKS in different concentrations promote proliferation of primary oral epithelial cells in vitro in a dose-dependent manner, demonstarting that both GEKG and KTTKS are effective in wound healing of oral mucosa.

Figure 7:
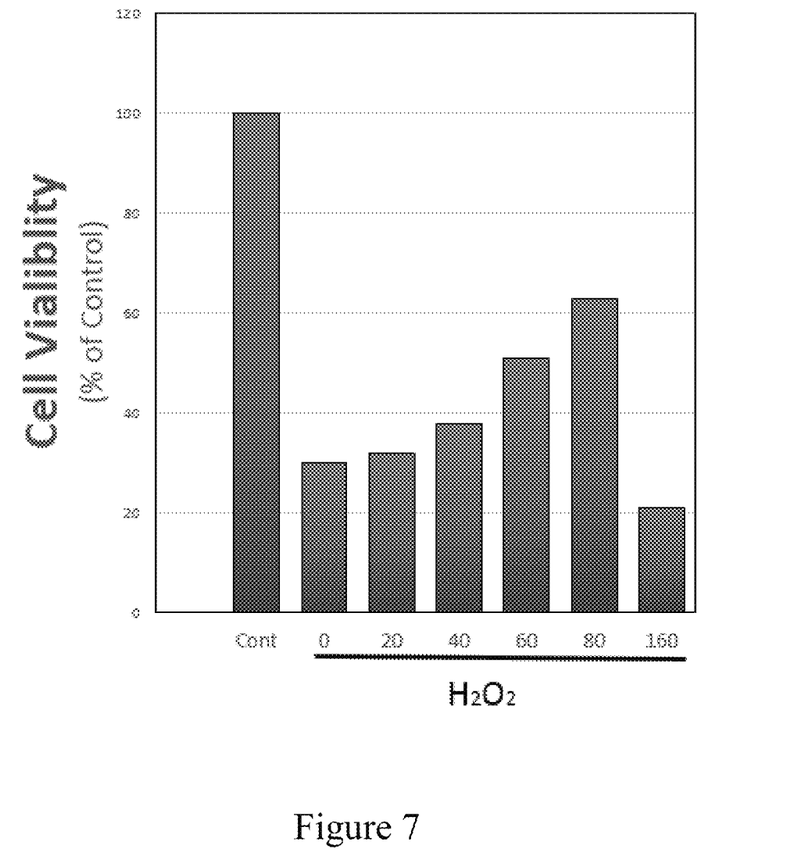
FIG. 7 shows an effect of GEKG and KTTKS in different concentrations in reducing death of oral epithelial cells induced by free radical $H_2O_2$ in vitro.

Example 5. Evaluation of GEKG and KTTKS in Reducing Death of Primary Oral Epithelial Cells Induced by Free Radicals and/or Inflammation FIG. 7 shows that both GEKG and KTTKS in different concentrations reduce death of primary oral epithelial cells induced by free radical $H_2O_2$ in vitro in a dose-dependent manner, demonstrating that both GEKG and KTTKS are effective in preventing death of primary oral epithelial cells and in turn in protecting oral epithelial cells, preventing oral mucosa lesions and oral cancers, and treating mouth ulcers.

Figure 8A:
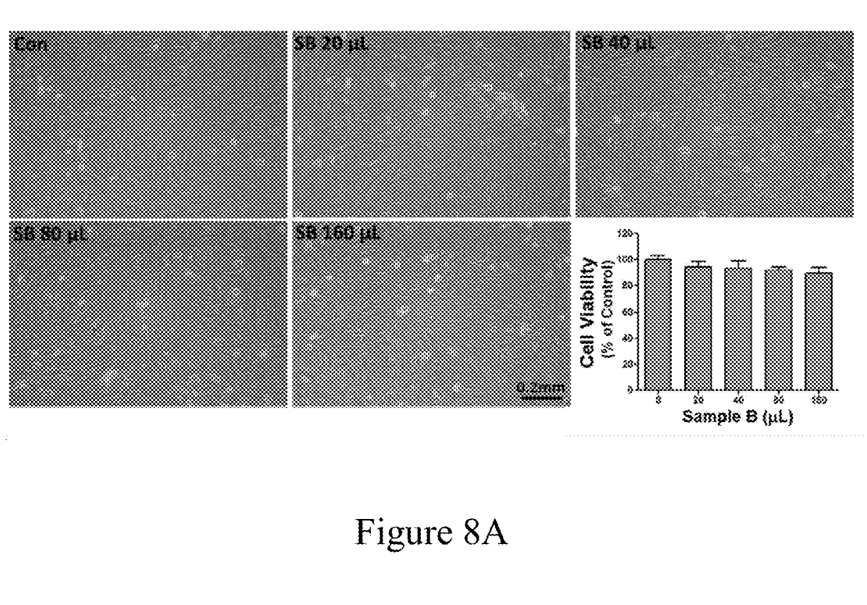
FIG. 8A shows an effect of GEKG and KTTKS in different concentrations in affecting proliferation of human gingival fibroblasts (HGF) in vitro.

Example 6. Evaluation of GEKG and KTTKS in Promoting Proliferation of Human Gingival Fibroblasts (HGF) and Production of Type I Collagen FIG. 8A shows that neither GEKG nor KTTKS in different concentrations exhibits a significant effect in promoting proliferation of HGF in vitro.

Figure 8B:
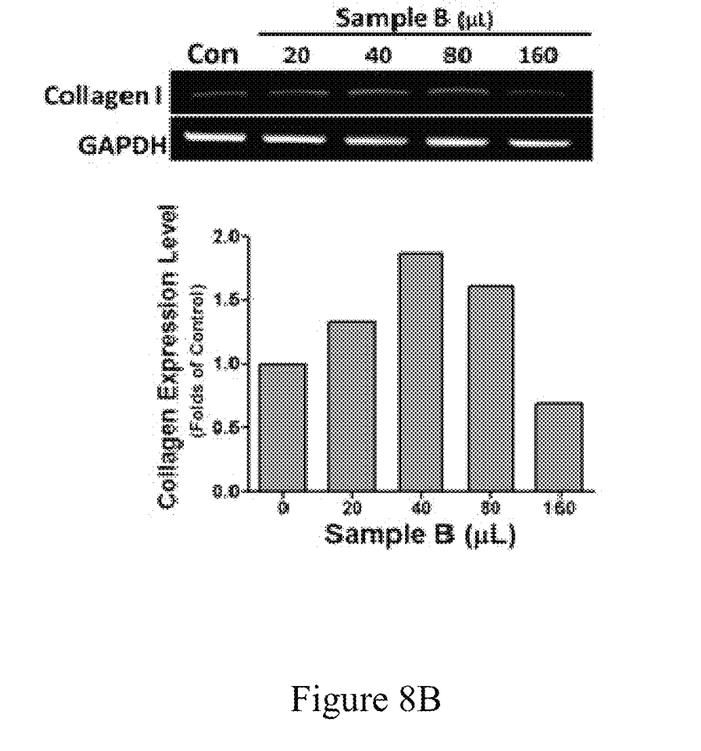
FIG. 8B shows an effect of GEKG and KTTKS in different concentrations in affecting production of Type I collagen in vitro.

In FIG. 8B, gel electrophoresis of RT-PCR products shows that the DNA bands of GAPDH and Type I collagen are located at a position of 467 bp and 409 bp, respectively, indicating that both GEKG and KTTKS stimulate gene expression of Type I collagen in transcription. Production of Type I collagen in human gingival fibroblasts was observed. There is a dose-dependent relationship between expression of Type I collagen and GEKG and KTTKS in a concentration of 0 to 40 μl.

It is demonstrated that an effect of GEKG and KTTKS in promoting proliferation of gingival Type I collagen results from stimulation or activation of human gingival fibroblasts rather than increase in an amount of human gingival fibroblasts.

Example 7. Evaluation of GEKG and KTTKS in Promoting Gene Expression of TGF-β1 in Human Gingival Fibroblasts (HGF)

Figure 9A:
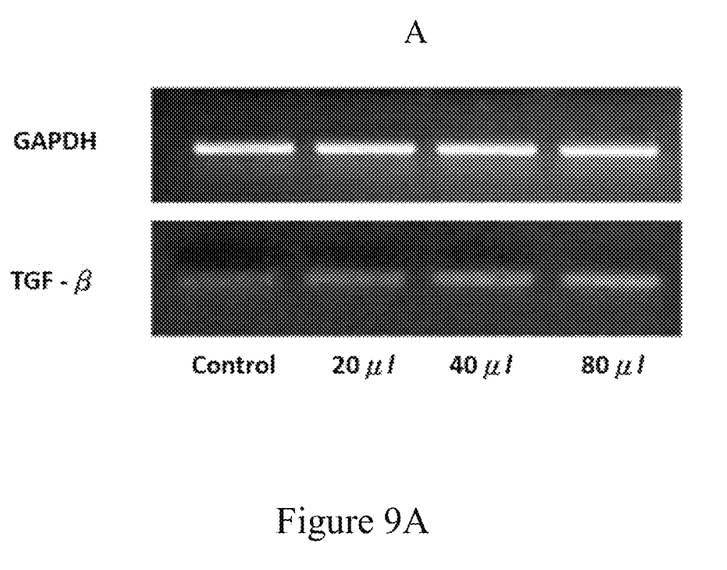
FIG. 9A shows gel electrophoresis of tumor growth factor-β1 (TGF-β1) and GAPDH as RT-PCR products.
Figure 9B:
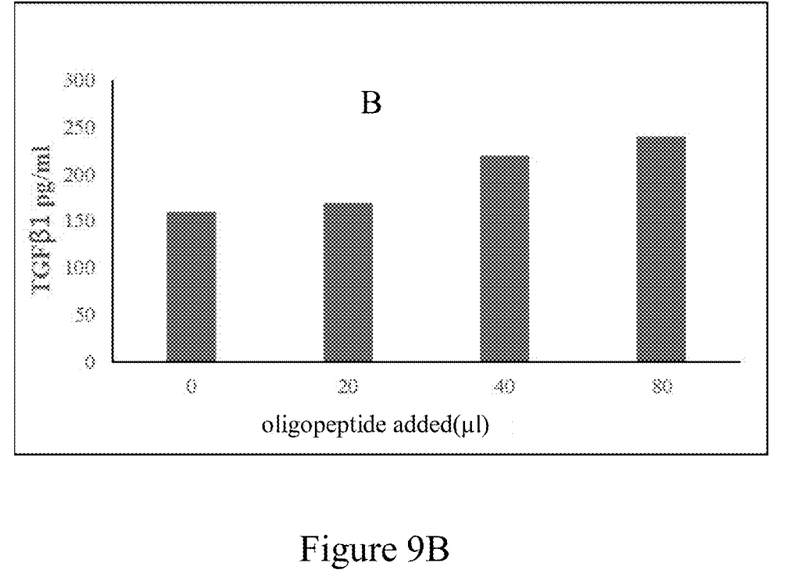
FIG. 9B shows an effect of GEKG and KTTKS in different concentrations in promoting expression of TGF-β1 in a dose-dependent manner.

It was well known in the art that TGF-β1 could regulate proliferation of gingival fibroblasts and osteoblasts, and promote synthesis of extracellular matrix (ECM) and Types I and III collagen.
Promotion of Gene Expression of TGF-β1 in Human HGF In Vitro
In FIG. 9A, gel electrophoresis of RT-PCR products shows that the DNA bands of GAPDH and TGF-β1 are located at a position of 467 bp and 161 bp, respectively, indicating that both GEKG and KTTKS stimulate gene expression of TGF-β1 in transcription.
FIG. 9B shows that there is a dose-dependent relationship between expression of TGF-β1 and a concentration of GEKG and KTTKS.
It was demonstrated that both GEKG and KTTKS could promote gene expression of TGF-β1 by stimulating human HGF.

Induction of Human HGF by TGF-β1 for Synthesizing Extracellular Matrix (ECM)
It is determined whether or not there exists synergism between GEKG or KTTKS and TGF-β1 in the synthesis of ECM when human HGF was treated with TGF-β1 (0.5 or 5 ng/ml) alone or in combination with KTTKS or GEKG (50 UM).

Human HGF were pre-cultured in the Dulbecco's Modified Eagle Medium (DMEM) containing 0.2% bovine serum for 24 hours, and then treated with 3 different concentrations (0, 0.5 and 5 ng/ml) of TGF-β1 for 24 hours, followed by further culturing for 24 hours in the absence of KTTKS and GEKG (solid line) or in the presence of 50 μM KTTKS or GEKG (dotted line).

Figure 10:
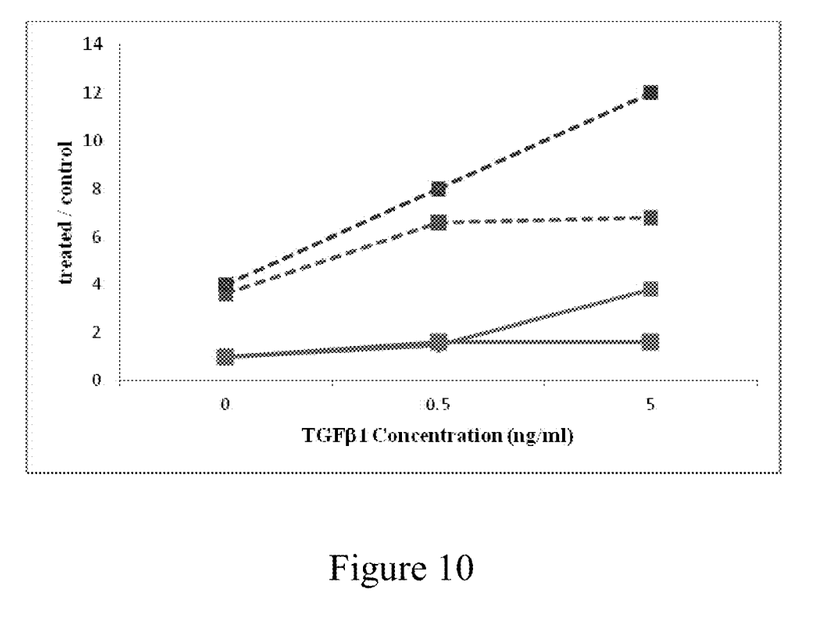
FIG. 10 shows induction of TGF-β1 and KTTKS or GEKG in the synthesis of extracellular matrix (ECM) from HGF.

FIG. 10 shows an amount of collagen and fibrin synthesized in the absence of KTTKS and GEKG (solid line) or in the presence of 50 μM KTTKS or GEKG (dotted line).

It was demonstrated that TGF-β1 and KTTKS or GEKG up-regulate biosynthesis of ECM in an independent manner, and KTTKS and GEKG exhibit a more significant ability in inducing human HGF for synthesizing ECM than TGF-β1. Another possible mechanism may be a synergism between GEKG or KTTKS and TGF-β1 in an increase of the biosynthesis of ECM.

Example 8. Preparation of a Gingiva-Repairing Lotion Comprising KTTKS or GEKG and Effect of the Gingiva-Repairing Lotion in Promoting Proliferation of Gingiva A gingiva-repairing lotion was prepared in accordance with the ingredients and their relative amounts as shown in the following Table 3.

TABLE 3

| Ingredients | Relative amounts (weight %) |
| --- | --- |
| KTTKS | 0.2 |
| GEKG | 0.2 |
| glycerol | 5 |
| sorbitol | 5 |
| EDTA•2Na | 0.1 |
| sodium benzoate | 0.5 |
| citric acid | 0.15 |
| peppermint oil | 0.08 |
| PEG-40 hydrogenated castor oil | 0.3 |
| deionized water | residual amount |

Weigh and add to an emulsification machine some deionized water, and keep the emulsification machine at a temperature of 20° C., followed by sequential addition of EDTA·2Na, sodium benzoate and citric acid in a weighed amount. The ingredients in the emulsification machine were homogeneously dissolved with an agitator, and then glycerol and sorbitol were sequentially added while keeping homogeneous agitation. A mixture of peppermint oil and PEG-40 hydrogenated castor oil was added to the emulsification machine and then homogeneously agitated, followed by addition of KTTKS and GEKG while keeping homogeneous agitation.

The gingiva-repairing lotion thus prepared was administered to mouth twice daily in an amount of 5 to 6 ml, and then spit out from mouth after a period of 10 to 15 minutes.

Figure 11:
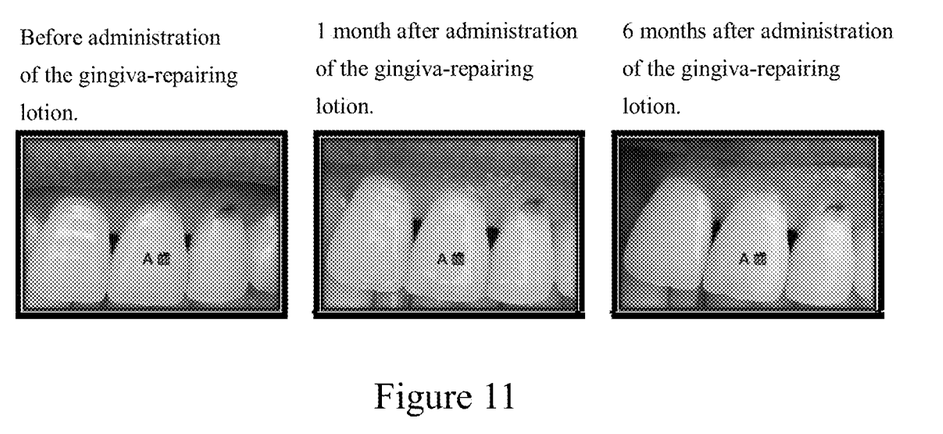
FIG. 11 shows gingiva proliferation after using a gingiva-repairing lotion comprising KTTKS or GEGK.

FIG. 11 shows that gingiva appeared in significant shrinkage before administration of the gingiva-repairing lotion; gingiva did not appear in shrinkage but in growth 1 month after administration of the gingiva-repairing lotion; and, gingiva appeared in significant growth and interdental space appeared in reduction 6 months after administration of the gingiva-repairing lotion.

It was demonstrated that the gingiva-repairing lotion is effective in stimulating growth of shrunk gingival.

```
                              SEQUENCE LISTING

Sequence total quantity: 1
SEQ ID NO: 1            moltype = AA  length = 6
FEATURE                 Location/Qualifiers
source                  1..6
                        mol_type = protein
                        organism = unidentified
PEPTIDE                 1
                        note = protein
SEQUENCE: 1
GKETSF                                                                      6
```

The invention claimed is:

1. A method for treating gingivitis and gingival atrophy and repairing oral mucosa in a subject, comprising a step of orally administering to the subject a lotion comprising a therapeutically effective amount of (i) an oligopeptide GEGK (SEQ ID NO: 1) or GEGKF (SEQ ID NO: 2), and (ii) an oligopeptide KTTKS (SEQ ID NO: 3) or KTTKSF (SEQ ID NO: 4), wherein G is glycine (Gly), E is glutamic acid (Glu), K is lysine (Lys), T is threonine (Thr), S is serine (Ser) and F is phenylalanine (Phe), wherein the oligopeptides GEKGF and KTTKSF are orally absorbed, and the oligopeptides GEKG and KTTKS are mucosally absorbed, and wherein the lotion comprises 0.2 to 2% by weight of GEKG or GEKGF and 0.2 to 2% by weight of KTTKS or KTTKSF, and does not comprise a gum health compound, a mucoadhesive compound or an amino acid.

2. The method of claim 1, wherein the oligopeptides GEGKF and KTTKSF are of sustained release.

3. The method of claim 1, wherein the lotion further comprises glycerol, sorbitol, EDTA, sodium benzoate, citric acid, peppermint oil, and PEG-40 hydrogenated castor oil.

* * * * *